United States Patent [19]
Reese et al.

[11] 4,138,478
[45] Feb. 6, 1979

[54] AGENTS FOR REDUCING THE DAMAGE TO HAIR DURING BLEACHING AND DYEING

[75] Inventors: Günter Reese, Düsseldorf; Erwin Weinrich, Haan; Edgar Lieske, Düsseldorf, all of Germany

[73] Assignee: Henkel Kommanditgesellschaft Auf Aktien (Henkel KGaA), Dusseldorf-Holthausen, Fed. Rep. of Germany

[21] Appl. No.: 738,475

[22] Filed: Nov. 3, 1976

[30] Foreign Application Priority Data

Nov. 4, 1975 [DE] Fed. Rep. of Germany ....... 2549294

[51] Int. Cl.$^2$ .................. A61K 7/06; A61K 7/13; A61K 7/135
[52] U.S. Cl. ..................... 424/62; 8/10.2; 8/11; 8/111; 252/186; 260/932; 424/DIG. 3; 424/70
[58] Field of Search ............ 424/62, DIG. 3, 70; 132/7; 8/10.2, 111; 252/186

[56] References Cited

U.S. PATENT DOCUMENTS

| 3,202,579 | 8/1965 | Berth et al. | 8/10.2 |
| 3,542,918 | 11/1970 | Berth et al. | 424/62 |
| 3,961,634 | 6/1976 | Busch | 132/7 |

Primary Examiner—Albert T. Meyers
Assistant Examiner—Vera C. Clarke
Attorney, Agent, or Firm—Hammond & Littell

[57] ABSTRACT

Compositions for changing the color of hair by the action (direct or indirect) of compounds therein which release nascent oxygen, do less harm to the hair when they have a content of a water-soluble 3-amino-1-hydroxypropane-1,1-diphosphonic compound. The compound can be in free acid or water-soluble salt or partial ester form. Hair which is pre-treated with one of the mentioned diphosphonic compounds is at least partially protected against the action of nascent oxygen.

14 Claims, No Drawings

AGENTS FOR REDUCING THE DAMAGE TO HAIR DURING BLEACHING AND DYEING

FIELD OF THE INVENTION

The present invention relates to compositions adapted to change the color of hair by the action (direct or indirect) of nascent oxygen, and particularly relates to such compositions containing an inhibitor of the damage which nascent oxygen in such compositions imparts to hair. The invention includes the application of the inhibitor to hair in a step preliminary to treatment of the hair with the color changing composition, and to hair which is protected against such attack by a content of the inhibitor.

In the present application the term "color changing compositions" includes hair bleaching compositions and hair dyeing compositions.

BACKGROUND OF THE INVENTION

It is present practice to bleach human and other hair by the action of agents which evolve active (i.e., nascent) oxygen. These agents decolorize the pigment in the hair. The agents which are the most commonly used for the purpose are hydrogen peroxide, sodium perborate, sodium persulfate, percarbamide, and melamine perhydrate, and their decolorizing action is direct. It is also present practice to employ these oxidizing agents in the dyeing of hair with dyes which develop their coloration by oxidation, to provide the necessary oxidation component. The action of the oxidizing agent in the hair coloration here is indirect.

A disadvantage of the aforesaid bleaching and dyeing processes is that the oxidizing agents used therein damage the substance of the hair to greater or less extent and so degrade it.

The damage which these oxidizing agents cause the hair is manifested by impairment of various properties of the hair such as its breaking strength, "feel" (akin to scroop), gloss and flexibility, so that the hair may actually become brittle. The agents increase the alkali solubility of the hair and this is the damage which is the most easily measurable. The damage is caused by the active (nascent) oxygen which these compounds evolve during their use on hair.

In the past, efforts have been made to find compounds which would mitigate or decrease the disadvantageous effects of the aforesaid oxidizing agents. Thus it has been proposed to add to hair bleaching and dyeing solutions certain 1-hydroxyalkane-1,1-diphosphonic acids and 1-aminoalkane-1,1-diphosphonic acids such as 1-hydroxyethane-1,1-diphosphonic acid, 1-aminoethane-1,1-diphosphonic acid, 1-aminobenzyl-1,1-diphosphonic acid or 1-hydroxyhexane-1,1-diphosphonic acid. Furthermore, aminopolyphosphonic acids having at least three phosphonic acid radicals in the molecule have been proposed for the purpose, such as aminotri-(1-ethyl-phosphonic acid), ethylenediaminetetra-(1-ethylphosphonic acid), aminotri-(1-propylphosphonic acid) and aminotri-(isopropylphosphonic acid). Even though these compounds have provided a considerable decrease in the damage to hair, a demand exists for compounds which will further reduce the damage to the hair in view of the increasing and more frequent use of oxidizing agents in bleaching and dyeing processes by hairdressers.

OBJECTS OF THE INVENTION

One object of the invention is to provide compositions which change the color of hair (either by bleaching or by dyeing) by the action of nascent oxygen, yet which will exert a milder degrading effect upon the hair than compositions which are presently available to the hair dressing art.

Another object is to provide such compositions in the form of fluid baths, dry powders, pastes and cream emulsions.

A further object of the invention is to provide a process for modifying the surface or the body of hair so as to render it more resistant to the action of nascent oxygen.

THE INVENTION

The foregoing objects are substantially attained by our discovery that compositions which are adapted to change the color of hair by the direct or indirect action of active (i.e., nascent) oxygen, possess a comparatively mild degrading effect upon the hair when they have a content of a diphosphonic compound selected from the group consisting of 3-amino-1-hydroxypropane-1,1-diphosphonic compounds of the formula:

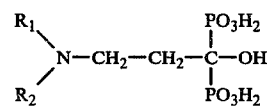

wherein $R_1$ and $R_2$ each represent H or $C_{1-3}$ alkyl, the water-soluble salts of said acids, and the water-soluble partial esters thereof.

We have made the additional surprising discovery that hair can be at least partially protected from attack by nascent oxygen by contacting it with an aqueous solution of one or more of the foregoing compounds. We have found that evidently these compounds are substantively adsorbed by hair and that when present on or in hair in this manner, they decrease the damage which would otherwise be caused by the nascent oxygen.

Particular importance is attached to 3-amino-1-hydroxypropane-1,1-diphosphonic acid and the water-soluble salts thereof, since these produce the best inhibitory effects observed to date.

The aminopropanediphosphonic acids described above are known as a group. They can be prepared by reacting β-alanine (or β-alanine appropriately alkylated on the nitrogen atom) with phosphorus trichloride and phosphorous acid. The reaction can be effected in the presence or the absence of an organic diluent.

Aminoalkanediphosphonic acids suitable for use in the compositions and processes of the present invention for reducing the damage to hair are, for example, 3-amino-1-hydroxypropane-1,1-diphosphonic acid, 3-dimethylamino-1-hydroxypropane-1,1-diphosphonic acid, 3-dipropyl-amino-1-hydroxypropane-1,1-diphosphonic acid, 3-methylamino-1-hydroxypropane-1,1-diphosphonic acid, 3-ethylamino-1-hydroxypropane-1,1-diphosphonic acid, and 3-iso-propylamino-1-hydroxypropane-1,1-diphosphonic acid. They can be used as free acids although, generally, they provide better protective action in the form of their alkali metal salts such as the sodium or potassium salts or in the form of their salts with water-soluble nitrogen bases, for example, ammonia, ethylamine, diethylamine, and ethanolamine. Water-soluble esters thereof (obtained by partial esterification of the acid groups or by esterification of the hydroxyl group) can also be used.

The aforesaid diphosphonic compounds can be applied in accordance with the present invention in admixture with a carrier substance which can be a gel. They can be applied as a component of a cream or a powder. They can be applied to the hair before the hair is bleached or dyed, or they can be applied as a component of a bleaching or dyeing composition which contains an oxidation agent, such as a water-soluble peroxide. The agents in accordance with the present invention can thus be added to compositions for pre-treating hair, such as rinsing or washing compositions.

The compositions of the present invention are applied to hair at any convenient pH, such as an alkaline pH. A pH in the range of 8–10 is preferred.

The aforesaid diphosphonic compounds in accordance with the invention are used in concentrations of from 0.01% to 10% and preferably 0.1% to 2%, by weight based on the weight of the composition as applied to the hair. Larger amounts can be used if desired. Such larger amounts are tolerated well by the hair and by bleaching and dyeing compositions, but such larger amounts provide virtually no advantage.

If desired, the compositions of the invention can also contain conventional quantities of additives commonly present in hair bleaching and dyeing compositions, such as perfume oils, dyes, thickening agents, fatty alcohols and wetting agents. Suitable thickening agents are cellulose derivatives, polyvinyl pyrrolidone, polyacrylates, alginates and, if required, fatty alcohols. Suitable wetting agents are fatty alcohol sulfates, fatty alcohol ether sulfates, alkyl sulfates, and products of condensation of fatty alcohols with ethylene oxide, the alkyl radicals in each case having a chain length in the range of 12 to 18 carbon atoms. Substances such as the $C_{12-18}$ alkylbenzene sulfonates and the $C_{12-18}$ alkylpyridinium salts are also suitable.

It appears that the diphosphonic compound is substantively adsorbed by the hair and acts to hinder degradation of the hair by nascent oxygen which is either present therewith or which is subsequently added.

Hair treated with color-changing compositions which contain a component which liberates nascent oxygen and which contain an inhibitor according to the present invention, is distinguished by a higher luster, better "feel" and particularly satisfactory resilience compared not only with hair which has been treated in a conventional manner, although under the same conditions, with compounds giving off active or nascent oxygen, but also with hair in which change of color was effected with the addition of previously proposed agents for reducing the damage to hair, such as 1-hydroxyethane-1,1-diphosphonic acid.

Differences in the extent of damage to hair are made numerically apparent by changes in the alkali solubility of the hair.

Even the bleaching effect and the covering of the grey when grey hair is dyed are promoted when the compositions contain the inhibitor agents of the present invention, as compared with the results obtained in comparative manner with compositions which contain previously proposed agents or which contain no inhibitory agent at all.

The invention is further illustrated by the examples which follow. These examples are best embodiments of the invention, and are not to be construed in limitation thereof.

EXAMPLE 1

The following illustrates the comparative effect of a typical diphosphonic compound of the present invention in inhibiting the hair alkali-solubilizing action of nascent oxygen in a conventional aqueous bleaching solution containing no other additive.

A 6% hydrogen peroxide solution was adjusted to pH 10 with ammonia. A sample of natural brown hair was immediately treated three times at intervals of 30 minutes with a portion of this solution without an additive as control. A similar sample of brown hair was simultaneously treated three times in succession with a portion of the solution to which had been added 0.1% by weight of 3-amino-1-hydroxypropane-1,1-diphosphonic acid. The procedure was simultaneously repeated with solutions to which 0.1% of 1-hydroxyethane-1,1-diphosphonic acid and ethylenediaminetetramethylene phosphonic acid had been added in the same amount.

The alkali solubility in weight percent of the hair before and after treatment was determined in each instance by the method of H. Freytag [Parfumerie und Kosmetik 41, No. 10, p. 405 (1960)]. The following values were obtained. The "% Incr." values are percentage points.

| Inhibitor Added | | Alkali Solubility | |
|---|---|---|---|
| Name | % | % by Wt. | % Incr. |
| [Untreated Hair | — | .6.6] | — |
| Control | — | 16.8 | 10.2 |
| 3-Amino-1-hydroxypropane-1,1-diphosphonic acid | 0.1 | 10.2 | 3.6 |
| 1-Hydroxyethane-1,1-diphosphonic acid | 0.1 | 12.8 | 6.2 |
| Ethylenediamine-tetra-methylene phosphonic acid | 0.1 | 12.4 | 5.8 |

The data show that the solution prepared by use of the 3-amino-1-hydroxypropane-1,1-diphosphonic acid provided an increase in efficacy of 42%, compared with the 1-hydroxyethane-1,1-diphosphonic acid of the prior art, and an increase in efficacy of 38% compared with the ethylenediaminetetramethylene phosphonic acid.

EXAMPLE 2

To determine the bleaching effected by the above solutions, samples of natural brown hair were treated for 30 minutes with each of the bleaching solutions given in Example 1, and were subsequently washed and dried. The bleaching effected in each instance was assessed visually and was rated on the following scale.
1 = Slight brightening.
10 = Considerable brightening.
The values obtained are given in the following table.

| Inhibitor Added | | |
|---|---|---|
| Name | % | Bleaching Effected |
| None | — | 4 |
| 3-Amino-1-hydroxypropane 1,1-diphosphonic acid | 0.1 | 8 |
| 1-Hydroxyethane-1,1 diphosphonic acid | 0.1 | 5 |
| Ethylenediamine-tetramethylene phosphonic | 0.1 | 6 |

| Inhibitor Added -continued | | |
|---|---|---|
| Name | % | Bleaching Effected |
| acid | | |

The data show that bleaching solutions containing inhibitor in accordance with the invention not only offer improved protection of the hair against damage by oxidation agents, but also provide an improved bleaching. In order to obtain the same bleaching, the quantity of oxidation agent can therefore be decreased or the duration of the bleaching can be shortened, which in turn leads to a further decrease in the damage done to the hair.

EXAMPLE 3

The following illustrates comparative effect of the inhibitors of the present invention in the dyeing of grey hair. Hair which was 90% grey was used. The extent to which the grey was concealed was visually assessed and was rated on the following scale.

1 = Slight concealment of the grey.
10 = Complete concealment of the grey.

For the dyeing, 100 parts by weight of a dyeing cream containing a conventional oxidation dye was mixed with 30 parts by weight of 6% aqueous hydrogen peroxide solution and the solution immediately used to dye a sample of the hair. For each comparison test a solution containing 0.2 parts by weight of one of the phosphonic acids was mixed into a sample of the cream. The samples of the hair dyed by this cream were then rated for concealment of the grey. The results are shown in the following table.

| Inhibitor Added | | |
|---|---|---|
| Name | % | Concealment of Grey |
| None | — | 4 |
| 3-Amino-1-hydroxy-propane-1,1-diphosphonic acid | 0.1 | 9 |
| 1-Hydroxyethane-1,1-diphosphonic acid | 0.1 | 6 |
| Ethylenediaminetetra-methylene phosphonic acid | 0.1 | 7 |

In addition to improving concealment of grey, the cream containing 3-amino-1-hydroxypropane-1,1-diphosphonic acid provided a dyed hair which was distinguished by a particularly attractive lustre and satisfactory "feel".

EXAMPLE 4

The following illustrates the preparation and use of a hair bleaching cream containing an organic agent which provides nascent oxygen and an agent according to the present invention which inhibits the harmful action of the cream towards hair.

8 parts by weight of a $C_{16-18}$ fatty alcohol mixture, 7 parts by weight of a $C_{16-18}$ alcohol sulfate mixture and 1 part by weight of a $C_{12-14}$ fatty alcohol mixture were melted together by heating to 80° C. The mixture was emulsified by rapidly stirring with 34 parts by weight of water of the same temperature. The emulsion was cooled, adjusted to pH 10.0 by addition of 4 parts by weight of concentrated ammonia solution made up to 100 parts by weight with water. For the purpose of bleaching, 100 g. of the cream was mixed with a mixture of 28 g. of melamine perhydrate and 2 g. of 3-amino-1-hydroxypropane-1,1-diphosphonic acid in the form of the sodium salt. The cream was uniformly distributed on natural brown hair, and a reaction period of 30 minutes was allowed. The hair was washed and dried. It was fully and uniformly bleached and was distinguished by a beautiful lustre and satisfactory "feel".

EXAMPLE 5

The following illustrates preparation and use of a paste bleaching agent containing an oxidizing agent and a diphosphonic agent according to the present invention as inhibitor for the nascent oxygen evolved therefrom. A bleaching agent in the form of a paste was prepared by mixing together 30 parts by weight of the reaction product of 1 mol of stearyl alcohol with 8 mol of ethylene oxide, 20 parts by weight of paraffin oil, 10 parts by weight of glycerine, 4 parts by weight of concentrated ammonia solution and 36 parts by weight of water. The transparent, viscous paste thus obtained was mixed with 5 g. of sodium perborate and 0.2 g. of 3-amino-1-hydroxypropane-1,1-diphosphonic acid and applied to natural brown hair. After 30 minutes the hair was bleached. It had a beautiful lustre, a satisfactory "feel" and satisfactory resilience.

EXAMPLE 6

The following illustrates the preparation and use of a hair bleach according to the present invention in free-flowing dry powder form.

A mixture was formed of 25 parts by weight of a $C_{12}C_{14}$ alkyl sulfate, 50 parts of soda (sodium carbonate), 20 parts by weight of sodium persulfate and 5 parts of a sodium salt of 3-amino-1-hydroxypropane-1,1-diphosphonic acid. The mixture was pulverized and the −50 + 200 mesh portion was removed. The fraction was a free flowing powder.

A portion of the powder was made up into a cream by addition of water and was applied to a sample of natural brown hair. After a reaction time of 30 minutes the hair was washed and rinsed. It was well bleached and had a very satisfactory hand. The procedure was repeated with a cream prepared in the same manner without however addition of the diphosphonic acid. The hair sample had a harsher hand.

The damage to the first sample of hair was considerably less than the damage to the second sample, and was substantially less than the damage produced by bleaches containing inhibitors of the prior art.

EXAMPLE 7

The following illustrates the preparation and use of a liquid bleaching agent according to the present invention wherein the inhibitor is present as an organic amine salt.

1 part by weight of a monoethanolamine salt of 3-amino-1-hydroxypropane-1,1-diphosphonic acid as inhibitor is dissolved in 80 parts of 10% hydrogen superoxide. The pH of the solution is adjusted to 10.0 by addition of monoethanolamine and the mixture is made up to 100 parts by weight with water. The damage to the hair when bleaching by means of this solution is substantially less than when an identical solution without the inhibitor is used, or when the same solution is used except that the inhibitor is replaced by a previously known agent.

EXAMPLE 8

The following illustrates a bleaching process according to the present invention wherein the inhibitor is first deposited on or absorbed into the hair and the hair is then bleached by the action of nascent oxygen in a second step.

Natural brown hair was pre-rinsed with a solution containing 10 parts by weight of the ammonium salt of 3-amino-1-hydroxypropane-1,1-diphosphonic acid, 10 parts by weight of cetyltrimethyl-ammonium chloride as wetting agent and 100 parts by weight of water; the time of contact was three minutes. The hair was then contacted with a 6% aqueous hydrogen peroxide solution having a pH of 10. The hair was then washed and dried, and was well bleached. With respect to resilience, lustre and feel, the hair thus bleached exhibited substantially better properties than hair which had been bleached in the same manner without the preliminary rinse.

We claim:

1. An aqueous composition adapted to change the color of hair by the action of nascent oxygen therein, said composition having water, an oxidizing agent and an effective content of a diphosphonic compound selected from the group consisting of aminopropane diphosphonic acids of the formula

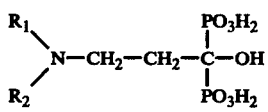

wherein $R_1$ and $R_2$ each represent H or $C_{1-3}$ alkyl, and the water-soluble salts thereof as an agent inhibiting the effect of said oxygen in degrading said hair.

2. The composition according to claim 1 having a pH in the range of 8–11.

3. The composition according to claim 1 wherein $R_1$ and $R_2$ are H.

4. The composition according to claim 1 wherein the water-soluble salts are selected from the group consisting of sodium, potassium, ammonium, and ethanolamine salts.

5. The composition according to claim 1 wherein the diphosphonic compound is present in amount between about 0.01% and 10% by weight.

6. The composition according to claim 1 wherein the diphosphonic compound is present in amount between about 0.1% and 2% by weight.

7. An aqueous alkaline bleaching solution containing 3% to 9% by weight of a water-soluble peroxide and 0.01% to 10% by weight of a diphosphonic compound selected from the group consisting of aminopropane diphosphonic acids of the formula

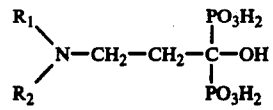

wherein $R_1$ and $R_2$ each represent H or $C_{1-3}$ alkyl, and the water-soluble salts thereof.

8. The solution according to claim 7 wherein the peroxide is hydrogen peroxide.

9. The solution according to claim 7 wherein the peroxide is sodium persulfate.

10. The solution according to claim 7 wherein the peroxide is melamine perhydrate.

11. A method of changing the color of hair which comprises rinsing said hair with an aqueous solution of a compound which releases nascent oxygen in said solution and an effective amount of a diphosphonic compound selected from the group consisting of aminopropane diphosphonic acids of the formula:

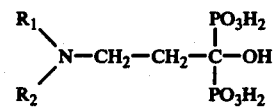

wherein $R_1$ and $R_2$ each represent H or $C_{1-3}$ alkyl, and the water-soluble salts thereof as an agent inhibiting the effect of said oxygen in degrading said hair.

12. A cream emulsion of the oil-in-water type for the treatment of hair, wherein the aqueous phase has a dissolved content of a compound providing nascent oxygen as hair bleaching component and 0.01% to 10% by weight of a diphosphonic compound selected from the group consisting of aminopropane diphosphonic acids of the formula:

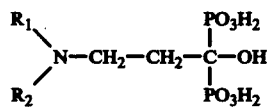

wherein $R_1$ and $R_2$ each represent H or $C_{1-3}$ alkyl, and the water-soluble salts thereof.

13. A method of protecting hair against damage by aqueous solutions having a dissolved content of an agent which releases nascent oxygen, which comprises pre-rinsing said hair with an effective amount of an aqueous alkaline solution of a diphosphonic compound selected from the group consisting of aminopropane diphosphonic acids of the formula

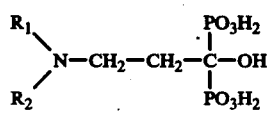

wherein $R_1$ and $R_2$ each represent H or $C_{1-3}$ alkyl, and the water soluble salts thereof.

14. The method according to claim 13 wherein rinsing is continued until the absorptive capacity of said hair for said diphosphonic compound is substantially satisfied.

* * * * *